United States Patent [19]

Smith et al.

[11] 4,361,548

[45] Nov. 30, 1982

[54] CONTACT LENS DISINFECTING AND PRESERVING SOLUTION (POLYMERIC)

[75] Inventors: Francis X. Smith; Thomas M. Riedhammer, both of Rochester, N.Y.

[73] Assignee: Bausch & Lomb Incorporated, Rochester, N.Y.

[21] Appl. No.: 210,960

[22] Filed: Nov. 28, 1980

[51] Int. Cl.$^3$ ............... A61K 31/74; A61K 31/14; A01N 33/12

[52] U.S. Cl. ............................. 424/78; 424/329

[58] Field of Search ......................... 424/78, 329

[56] References Cited

U.S. PATENT DOCUMENTS

| | | | |
|---|---|---|---|
| 3,288,770 | 11/1966 | Butler | 260/88.3 |
| 3,539,684 | 11/1969 | Hoover | 424/78 |
| 3,639,576 | 2/1972 | Kaspar et al. | 424/78 |
| 4,013,576 | 3/1977 | Loshaek | 424/78 |
| 4,029,817 | 6/1977 | Blanco et al. | 424/80 |
| 4,127,423 | 11/1978 | Rankin | 424/127 |

FOREIGN PATENT DOCUMENTS

| | | |
|---|---|---|
| 870556 | 5/1971 | Canada . |
| 2916698 | 8/1979 | Fed. Rep. of Germany . |
| 2027040 | 2/1980 | United Kingdom . |

OTHER PUBLICATIONS

CTFA Cosmetic Ingredient Directory, the Cosmetic, Toiletry & Fragrance Assoc., 2nd ed. under heading Quaternium-40.

*Primary Examiner*—Douglas W. Robinson
*Attorney, Agent, or Firm*—Robert M. Phipps

[57] ABSTRACT

A disinfecting and/or preserving solution for contact lenses is disclosed. The disinfecting solution is an aqueous solution containing 0.00001 to 0.1 weight percent of a dimethyldiallylammonium chloride homopolymer having a molecular weight from about 10,000 to about 1,000,000, optionally together with up to 0.5 weight percent of ethylenediaminetetraacetic acid or other enhancers and optional buffers and the like.

4 Claims, No Drawings

CONTACT LENS DISINFECTING AND PRESERVING SOLUTION (POLYMERIC)

BACKGROUND

1. Field of the Invention

This invention relates to the use of dimethyldiallylammonium chloride homopolymers as the active antimicrobial agent in disinfecting and/or preserving solutions for contact lenses.

2. Description of the Prior Art

This invention relates to disinfecting and preserving contact lenses, particularly soft contact lenses. When the term "soft contact lenses" is used herein, it is generally referring to those contact lenses which readily flex under small amounts of force and return to their original shaped when released from that force. Typically, soft contact lenses are formulated from poly(hydroxyethyl methacrylate) which has been, in the preferred formulations, crosslinked with ethylene glycol dimethacrylate. For convenience, this polymer is generally known as PHEMA. Soft contact lenses are also made from silicone polymers typically crosslinked with dimethyl polysiloxane. As is known in the art, conventional hard lenses, which cover only the cornea of the eye, usually consist of poly(methylmethacrylate) crosslinked with ethylene glycol dimethacrylate.

Hard contact lenses do not absorb appreciable amounts of water as do some soft contact lenses and thus the use of harsher disinfecting and cleaning agents does not create a problem in the hard contact lenses cleaning area. However, many hard lens disinfecting and preserving solutions contain benzalkonium chloride or chlorobutanol which may render the treated lenses hydrophobic, may not be stable in solution or lack compatibility with certain types of hard lenses, e.g., high silicone content. As is generally known, the users of soft contact lenses are warned against using solutions made for hard contact lenses since the materials in the solutions, as mentioned, may be absorbed or even concentrated by the soft contact lenses and may seriously damage the soft contact lenses or the eye of the user.

U.S. Pat. No. 3,288,770, G. B. Butler, discloses water soluble quaternary ammonium polymers including solid polymers of dimethyldiallylammonium chloride. These polymers are mentioned at column 10 as having utility as spinning aids for textile materials, antistatic agents for textile materials, bacteriostatic and fungistatic agents, wet strength improvement agents for papers and other textile aids, as accelerators for curing rubber and as curing agents for epoxy resins and as stabilization and regulation agents for particle size in suspension polymerization and surface active agents. Thereafter considerable discussion is given to the use of these polymers as flocculating agents.

U.S. Pat. No. 3,539,684, M. F. Hoover, discloses bactericidal effects of various homopolymers and copolymers of fatty quaternary diallylammonium compounds. The use of dimethyldiallylammonium chloride as a comonomer does not reduce the effectiveness of the polymerized fatty quaternary monomer. There is no suggestion or teaching that polymeric dimethyldiallylammonium chloride has bacterial activity or synergistic effect. The fatty quaternary polymers and copolymers are stated to be useful in treating circulating water systems and swimming pools and other bodies of stagnant water to inhibit algae and bacteria.

U.K. patent application No. 2,027,040A discloses the use of water soluble terpolymers of diallylamine quaternary salts as sterilizing agents for contact lenses. The application teaches that each of the three types of monomers must be present in order to obtain an effective eye care solution. The N-substituents for each class of monomers are respectively (A) low-low, e.g., dimethyl, (B) low-medium, e.g., methyloctyl and (C) low-higher, e.g., methyllauryl or methylcetyl, in molecular size; B:C being usually 5:1 to 0.333:1 (preferably 2:1 to 1:1) in weight ratio, and species less than 10,000 or preferably 20,000 m.w. usually being removed, have surprisingly effective sterilizing activity, e.g., against Candida while (a) not accumulating in soft contact lenses, whereby they can be used as an overnight, non-irritant, aqueous, sterilant solution at concentrations below 0.1 weight percent, e.g., 0.05 or less and (b) not penetrating skin or like membranes whereby aqueous formulations can be used as topical disinfectants without systemic side effects.

SUMMARY OF THE INVENTION

In accordance with this invention, there is provided an aqueous solution for preserving and/or disinfecting contact lenses having as the active antimicrobial agent dimethyldiallylammonium chloride homopolymer having a molecular weight from about 10,000 to 1,000,000 present in an amount from about 0.00001 to about 0.1 weight percent of said composition. Typically the solution will be an isotonic solution and optionally contains enhancing or conditioning agents.

DESCRIPTION OF THE PREFERRED EMBODIMENTS

Applicants have discovered that contact lenses can be effectively disinfected and preserved with dilute aqueous solutions of dimethyldiallylammonium chloride homopolymer (hereafter, for convenience, referred to as DMDAAC). More particularly it was found that advantageous results are obtained when the DMDAAC is present in an amount from 0.00001 to 0.1 weight percent. Preferably the DMDAAC, when used without an enhancer, which is hereinafter described, the concentration is from about 0.0004 to about 0.02 weight percent. When in combination with an enhancer, the DMDAAC antimicrobial agent of this invention can be present in an amount from about 0.00001 to about 0.1 weight percent and more preferably from 0.0001 to 0.02.

DMDAAC is listed in the CTFA Cosmetic Ingredient Directory, the Cosmetic, Toiletry and Fragrance Association, Washington, DC (2nd Edition) under the heading Quaternium-40. Another name shown for DMDAAC is Merquat-100, a trademark of Merck & Co., Inc. who offer the polymer for hair and skin applications. In the same directory Quaternium-41 is disclosed as the polymeric quaternary ammonium salt of acrylamide and dimethyldiallylammonium chloride monomers. Quaternium-41, while closely related to DMDAAC, was not found to be effective in the present invention. Quaternium-41 is also suggested for skin care products.

The antimicrobial effect of DMDAAC can be enhanced or increased by the use of an enhancer. An enhancer can be present in an amount from zero to about 0.5 weight percent and preferably from about 0.0001 to about 0.1 weight percent. Suitable enhancers are selected from the group which includes thimerosal, sorbic acid, phenylmercuric salts (e.g., nitrate, borate, acetate or chloride), ethylenediaminetetraacetic acid (EDTA) and its salts and mixtures of the foregoing enhancers. A particularly preferred enhancer is EDTA used in an amount from 0.01 to about 0.2 weight percent.

A typical composition of the present invention may contain, in addition to the active ingredients described earlier, buffers, cleaners, stabilizers and isotonic agents which aid in making the ophthalmic composition more comfortable to the user. These additional materials must be non-toxic and must not distort the lens.

Suitable buffers include sodium or potassium citrate, citric acid, boric acid, sodium bicarbonate and various mixed phosphate buffers including combinations of $Na_2HPO_4$, $NaH_2PO_4$ and $KH_2PO_4$. Generally, buffers may be used in amounts ranging from about 0.05 to 2.5 and preferably 0.1 to 1.5% (w/v).

Non-ionic surfactants suitable for use as cleaners include neutral polyoxyethylene fatty acid (available under the tradename Myrj 52), polysorbate 80 (tradename Tween 80) and polyethyleneglycol ether of lauryl alcohol (tradename Brij 35). These cleaners can be added in amounts ranging from 0.01 to 15 weight percent and preferably about one weight percent.

The treating solution for contact lenses is typically maintained at an osmotic pressure similar to that of physiological saline, i.e., substantially isotonic, or equivalent to 0.9% saline, or with suitable agents alone or in combination to render the solution substantially isotonic. Hypotonic solution, e.g., tap water, may cause the lens to adhere tightly to the cornea while hypertonic solutions (excess saline) may result in stinging, lacrimation and a red eye.

The method of use of the solution comprises having the wearer of the contact lenses remove the lenses from the eyes. Then the lenses are rubbed with preserved cleaning solution, rinsed with preserved saline solution and placed in a suitable container with a sufficient amount of the composition of the instant invention to cover the lenses. The lenses are allowed to soak preferably for a period of from about 4 hours to about 12 hours at room temperature. The lenses are then removed from the solution, washed with saline solution and then replaced on the eyes.

The following examples are illustrative only and should not be construed as limiting the invention. All parts and percentages referred to herein are on a weight per volume basis. The saline solution used in the examples is an isotonic, buffered saline solution unless otherwise specified.

EXAMPLE I

Preserved Saline Solution

Saline solutions containing the indicated amounts of DMDAAC (Merquat-100 brand) and enhancer are prepared. The homopolymer has an average molecular weight of $10^5$–$10^6$. Each solution is exposed to approximately 1,000,000 microorganisms per ml of the indicated organism. The solution is considered effective if the concentration of *Pseudomonas aeruginosa* or *Staphylococcus aureus* is reduced to less than 0.1% of the initial concentration within 14 days and *Apergillus niger* is maintained at its original level. In this example the enhancer used is disodium EDTA. The solutions are evaluated as indicated in Table I below.

TABLE I

| | SOLUTION | |
|---|---|---|
| | A | B |
| Amount DMDAAC | 0.0004 | 0.002 |
| Amount Enhancer | 0.1 | 0.1 |
| Exposure Results[1] | | |
| *S. aureus* | ++ | ++ |
| *P. aeruginosa* | ++ | ++ |
| *A. niger* | ++ | ++ |

[1] ++ = Effective
+ = Marginal
NE = Not effective

EXAMPLE II

Preserved Cleaner

A surfactant cleaner for lens cleaning containing 0.1% of a neutral polyoxyethylene fatty acid non-ionic surfactant (sold under the trademark Myrj 52 by Atlas Powder Co.) is used in this comparison. To the cleaner is added the indicated amount of DMDAAC. No enhancer is added to the cleaner. The effectiveness against *P. aeruginosa* is determined as in Example I. The solution is considered effective against *Candida albicans* if its concentration remains at or below the initial concentration of 1,000,000 microorganisms per ml for 14 days. The cleaner is effective.

EXAMPLE III

Disinfecting Solution

An isotonic disinfecting solution for soft contact lenses is prepared in which the antimicrobial agent is DMDAAC. The solution also contains an enhancing agent when so indicated. The solution is exposed to approximately 1,000,000 microorganisms per ml for six hours. The solution is considered effective if there is at least a 99.9% reduction of the viable microorganism. The solutions are prepared and evaluated as indicated in Table II below.

EXAMPLE IV

Disinfecting Regimen

Two isotonic solutions, one containing 0.02 weight percent DMDAAC and the other containing 0.01 weight percent DMDAAC and 0.002 weight percent thimerosal are evaluated in a disinfecting regimen for soft contact lenses. Both solutions are found to be effective since the regimen completely removes from the lenses or kills the six pathogenic challenge organisms recommended by the U.S. Food and Drug Administration.

The foregoing examples and methods have been described in the foregoing specification for the purpose of illustration and not limitation. Many other modifications and ramifications will naturally suggest themselves to those skilled in the art based on this disclosure. These are intended to be comprehended as within the scope of this invention.

TABLE II

| SOLUTION | AMOUNT DMDAAC | ENHANCER[1] | AMOUNT ENHANCER | EXPOSURE RESULT[2] | | |
|---|---|---|---|---|---|---|
| | | | | *S. epidermids* | *C. albicans* | *A. fumigatus* |
| A | 0.02 | EDTA | 0.2 | ++ | NE | NE |
| B | 0.02 | — | — | + | NE | NE |

TABLE II-continued

| SOLUTION | AMOUNT DMDAAC | ENHANCER[1] | AMOUNT ENHANCER | EXPOSURE RESULT[2] S. epidermids | C. albicans | A. fumigatus |
|---|---|---|---|---|---|---|
| C | 0.02 | EDTA<br>SORB | 0.2<br>0.1 | * | NE | NE |
| D | 0.02 | EDTA<br>SORB | 0.01<br>0.1 | * | NE | NE |
| E | 0.02 | EDTA<br>SORB<br>THIM | 0.01<br>0.1<br>0.002 | * | ++ | ++ |
| F | 0.02 | EDTA<br>SORB<br>THIM | 0.2<br>0.1<br>0.002 | * | ++ | + |
| G | 0.02 | EDTA<br>THIM | 0.01<br>0.002 | * | ++ | NE |
| H | SALINE CONTROL | | — | NE | NE | NE |

[1]EDTA = Disodium EDTA
THIM = Thimerosal
SORB = Sorbic Acid
[2]++ = Effective
+ = Marginal
NE = Not Effective
* = Not Tested The embodiments of the invention in which an exclusive property or privilege is claimed are defined as follows:

1. An aqueous solution for preserving or disinfecting soft contact lenses having as the active antimicrobial agent dimethyldiallylammonium chloride homopolymer, having a molecular weight from about 10,000 to 1,000,000, present in an amount from about 0.00001 to about 0.1 weight percent of said composition.

2. The composition of claim 1 wherein the amount of homopolymer is from about 0.0004 to about 0.02 weight percent.

3. A method of disinfecting contact lenses comprising contacting the lenses for a sufficient time to disinfect the lenses with the aqueous solution of claim 1.

4. A method of inhibiting microorganism growth when sterilized contact lenses are stored in a solution comprising storing the lenses in the aqueous solution of claim 1.

* * * * *